United States Patent [19]

Fernandez

[11] Patent Number: 4,942,153

[45] Date of Patent: Jul. 17, 1990

[54] SKIN MOISTURIZING PRODUCT AND PROCESS

[76] Inventor: Helen M. Fernandez, 20938 Bandera St., Woodland Hills, Calif. 91364

[21] Appl. No.: 10,225

[22] Filed: Feb. 3, 1987

[51] Int. Cl.$^5$ .................... A61K 37/12; A61K 35/28
[52] U.S. Cl. .......................... 514/2; 514/21; 514/847; 514/801; 424/195.1
[58] Field of Search .................... 514/2, 21, 801, 846, 514/847; 424/195.1

[56] References Cited

U.S. PATENT DOCUMENTS

| 3,991,184 | 11/1976 | Kludas et al. | 514/21 |
| 4,255,418 | 3/1981 | Bailey | 424/145 |
| 4,322,020 | 3/1982 | Stone | 222/95 |
| 4,416,873 | 11/1983 | Puchalski et al. | 424/70 |
| 4,597,963 | 7/1986 | Deckner | 424/59 |
| 4,695,456 | 9/1987 | Wilder | 424/94.5 |
| 4,722,843 | 2/1988 | Vinson | 514/847 |

FOREIGN PATENT DOCUMENTS

| 0076442 | 6/1977 | Japan | 514/21 |
| 0089410 | 5/1985 | Japan | 512/2 |
| 0116617 | 6/1985 | Japan | 514/801 |

OTHER PUBLICATIONS

Radulescu et al., "Hexestrol Acetate for the Treatment of Dystrophic Vaginitis", CA102:12396w, 1985.

*Primary Examiner*—Johnnie R. Brown
*Assistant Examiner*—Jean C. Witz
*Attorney, Agent, or Firm*—David O'Reilly

[57] ABSTRACT

A moisturizing product and process designed to let a user quickly and easily rehydrate and moisturize the skin at their convenience, at anytime and any place. The fomulas are a combination of purified water, with a soluble collagen and other products to be applied to treat dry skin to slow the damaging effect of sun, wind, polutents and toxins. Further, the solution of the formula has a Deionized Water and soluble collagen in combination with other additives is applied to the skin by means of a spray in a very fine mist. When the formula reaches the skin it begins to rehydrate the cells of the skin by binding the water to the skin with the collagen in the formula. The cells of the skin exposed to a harsh drying environment are replenished and rehydrated by the fine spray mist.

12 Claims, No Drawings

SKIN MOISTURIZING PRODUCT AND PROCESS

FIELD OF THE INVENTION

This invention relates to a new moisturizing skin product and process, and more particularly relates to a moisturizing skin process and method which allows the product to be sprayed on the skin.

BACKGROUND OF THE INVENTION

In recent years, scientists and researchers involved in the study of skin ageing have agreed that moisturizing will improve the feel and texture of the skin, and help to stall the formation of wrinkles due to dry skin. Moisturizing also combats a slow decline in the skin's natural water managing capacity and skin can remain more faithful to its function as a barrier when it is moisturized.

A good skin moisturizer also can minimize the effects of ageing on your skin. Moisturizing is a step which will protect your skin against the effects of external environmental factors. The skin has highly specialized two-layer structure which is constantly regenerating itself. The outermost layer is called the epidermis and is composed of flat "dead" skin cells that contain the protein keratin, plus a deep layer of living cells. When the skin is healthy the living cells move to the surface in a continual two-to-four week cycle, and form a protective layer called the stratum corneum. As new cells are generated in the lower level of the epidermis, the top older cells harden and die. These cells are then shed from the surface of the skin as microscopic flakes. As skin matures, cell renewal takes much longer and needs ever increasing moisture to protect against external factors.

All types of skin need some moisturing but the face, which is constantly opposed to the elements, can cause important moisture loss through evaporation. Moisturizes help the top layer of the skin retain its natural water content by providing ingredients that attract water and seal it into the top layers of the skin. Further, moisturizers condition the texture of the skin minimizing the appearance of lines and small wrinkles that form when the skin dries out. This outer layer of cells is the layer that is of interest to us.

After years of study and experience water has gained favor and is now recognized as the best and most effective moisturizer available, as it most closely resembles the natural moisture of the skin. Dermatologists have known for years the many benefits of using water to replenish precious moisture lost. While aware of this fact the methods of moisturizing were often cumbersome and messy.

Recent studies of genetics and cell structure have shown that a protein reportedly slows the aging process by helping the skin to retain moisture. Such products take the form as creams which are spread on the skin to help the skin retain the moisture. These products are in the form of emollients, and creams which in some cases are applied to the skin and left on overnight. Others are rubbed into the skin to retain moisture during the day. A problem with these particular products is that some are extremely expensive, and most are inconvenient and messy to apply. It would be advantageous if a product were available that could be easily applied anywhere, anytime, night or day, to instantly help in moisturizing and retaining moisture in the skin.

It is therefore, one object of the present invention to provide a unique method of applying and binding moisturizing water to the skin.

Another object of the invention is to provide a unique product which will moisturize the skin, in addition to aiding in retaining the moisture.

Yet another object of the present invention is to provide a unique method and product for applying nature's best moisturizer with the added benefits of using a collagen to bind the moisture in the skin.

Yet another object of the present invention is to provide a product comprised of a mixture of water with a small amount of collagen to provide a unique product and method for moisturizing the skin.

BRIEF DESCRIPTION OF THE INVENTION

The purpose of the present invention is to provide a skin moisturizer for applying nature's best moisturizer which includes the added benefits of using a collagen to bind the moisture in the skin which can be conveniently applied anytime, anywhere—purified.

These purposes are realized by mixing a collagen with water to allow it to be easily sprayed onto the skin. Collagen is the fibrous protein in the dermis (the layer of cells just below the surface of the skin) that gives the skin its firmness and resiliency. Collagen has been found to act as a binding agent with water, which traps moisture against the skin cells without clogging or contaminating the pores of the skin. The product and method disclosed herein can help to speed cell turnover and keep young fresh cells moisturized to perhaps somewhat slow the decline in aging of the skin. With the product and process of the present invention skill cells are allowed to absorb and retain the renewing benefits of water.

The present invention is comprised of a collagen which is an animal extract in propylene glycol water at a 50—50 ratio. This collagen is soluable in water in almost any proportion. The formula for the product is to add approximately one to two percent collagen with Deionized Water in approximately each eight ounces of the formula. A small amount of approximately 0.3% to 0.5% DMDM Hydantoin is also added to the formula as a preservative. This is a formula for moisturizing most normal skins and can be used by all.

An alternative formula adds a cucumber extract sometimes known as Cucumber HS, extract of cucumber, or Cucumus Satibus Extract. This particular formula is considered useful for people with oily and/or blemished skin condition. The formula is the same as before having one to two percent collagen, combined with one to two percent cucumber extract in addition to 0.3% to 0.05% DMDM Hydantoin preservative with the balance being Deionized Water to make up eight ounces of product.

The unique method of applying the product is by a very fine spray, or mist. Preferably only Deionized Water is used eliminating any minerals or contaminants from reaching the skin. The formula is sprayed on the skin in a very fine mist using a constant pressure sprayer, such as a Calmar Mark 11 Sprayer manufactured by Calmar Dispensing Systems, 40 Sterling Road, Watchung, NJ., 07060. This particular sprayer is preferable because it produces a very fine uniform spray pattern. Further, the spray uses a non-throttling system preventing dripping or jetting however stroked. The delivery volume is approximately 0.14 cc (cubic centimeters) per stroke, through an orifice measuring 0.012 inches. The combination of pure ingredients with the use of this accurate fluid misting sprayer, assures the user of a dripless fine mist delivery of uncontaminated solution to dry skin.

The above and other novel features and advantages of this invention will be more fully unerstood from the following detailed description.

DETAILED DESCRIPTION OF THE INVENTION

The formula disclosed herein of Deionized Water and collagen when sprayed create an atmosphere conducive to the growth and development of new, fresh skin cells. In addition, the formula when sprayed on the skin rehydrates dry cells already present on the surface of the skin. Water is widely accepted as nature's best moisturizer and is the best moisturizer available. The use of a collagen in the formula assists in binding the water to the surface of the skin cells without clogging or contaminating the pores of the skin.

Unlike the various expensive moisturizing creams or topical ointments presently available the formula disclosed herein allows the user to apply the needed moisturizer at any time. There are no messy creams to apply and the moisturizing product disclosed herein can be applied when it is needed most. After work, at play or exercise, the moisturing formula can be quickly and easily sprayed in a convenient easy manner, using a spray bottle such as the Calmar Mark 11 referred to hereinabove. Skin can be rehydrated immediately without the need for a sink, mirror, bathroom, water source or towels. In addition, the formular is economical and affordable as only a small amount of the very expensive collagen thoroughly mixed with the water solution is needed eliminating the need for applying large amounts of expensive creams. The proper amount is easily dispensed with each stroke of the pumping system.

The invention involves the use of several separate formulas, one is a formula employing a collagen in combination with a purified water for use on normal and all types of skin conditions. A second formula is provided for people who have very oil and/or blemished skin conditions. The latter formula was created primarily for men, the majority of which have oily skin conditions, it provides moisture for an often dehydrated oily complexion. A third formula is provided for use by people with extremely dry or rough skin conditions. This combination or formula performs an enriched moisture.

A general all purpose formula by weight is as follows:
1. 98.7% Deionized water.
2. 1.0% Soluble Animal Collagen (Bovine)
3. 0.3% DMDM—Hydantoin Where the products are:

Deionized Water—neutral ph, without minerals or other contaminants.

Soluble Collagen—protein fiber found in skin and is a collagen extracted from bovine tissue.

DMDM Hydantoin—organic preservative.

The first specific formula which can be used by everyone and can stand alone or work with almost any skin care program and is effective and safe for all types of skin. This Formula is comprised of a collagen sometimes known by the trademark name Actigen C, which is an animal extract in propylene glycol water 50—50. This collagen is a protein fiber found in the skin which helps build water level by holding moisture-filled fibers close to the skin's surface. The collagen, it is believed, produces younger looking more supple skin due to increased moisture retention and content. The collagen, it is believed, works to decrease lines and wrinkles caused by lack of moisture. The collagen used is an extract produced from bovine tissue.

Further, the collagen is soluble in water at any proportions and preferably has a pH of 4.5 to 7.0 and a specific gravity of 1.02 to 1.15, at approximately 25 degrees centigrade. Also, the collagen should have a microbrial count of less then 100 organisms per gram.

This particular formula for use on all skin care programs is comprised of:
1. 1%–2% Collagen.
2. 0.03%–0.05% DMDM Hydantoin (organic preservative).
3. Balance of Deionized Water to complete approximately eight ounches of formula.

The percentages given are by weight of the product rather then by volume.

A second formula created especially for people with a rather oily skin conditions, which applies primarily to men, can provide moisture for often dehydrated oily complexions. This formula is substantially the same as that listed above, but with the addition of a extract of cucumber known by the common names Cucumber HS, Extract of Cucumber, Cucumus Sativus Extract. It is also known by the trademark name of Actiphyte of Cucumber. The major constituent of the cucumber extract is 96% water. This moisturizing formula is comprised of;
1. 1% to 2% collagen.
2. 1% to 2% cucumber extract, described hereinabove.
3. 0.03% to 0.05% DMDM Hydantoin.
4. Balance of Deionized water to produce eight ounces of formula.

The later formula as described above utilizes the cucumber extract which assists in moisturizing the skin of people with oily and/or blemished skin conditions. This particular form was created primarily for men, the majority of which have an oily skin condition, it provides and retains moisture for often dehydrated oily complexions.

The third formula includes a product which prepares the skin for moisture. This product is known by the common name of Panthenol providing a lubricating moisture-building blend to the collagen and Deionized Water to smooth lines and reduce visual effects of aging. This particular formulation was produced particularly for people with extremely dry or rough skin conditions, this combination of compounds forms an enriched moisture. The formula utilizes a product known by the trademark name Dexpanthenol, which is prepared by the addition of propanolamine to optically active a, v-dihydroxy-$\beta$-$\beta$-dimenthylbutyrolactone known by the common name Panthenol and is a viscouse somewhat hygroscopic liquid. The product is generally in the form of a white powder freely soluble in water and has a natural pH of about 9.5. The formula is as follows:
1. 1% to 2% collagen.
2. 0.5% to 1.5% Panthenol.
3. 0.03% to 0.05% DMDM Hydantoin.
4. Balance of Deionized Water to complete eight ounces of formula.

These formulas once mixed remain substantially clear and light in texture and are retained in an extra fine mist allowing full absorbtion by the skin when sprayed on. The advantage of the particular formulas described are that they allow the user to replenish and rehydrate dry damaged skin at anytime, anywhere. The product also allows a convenient method of applying nature's best moisture with a collagen binder without the use of messy creams and ointments. The collagen found in the formulas listed above act as a binding agent between skin cells and clear contaminated-free Deionized or pure water. Further, a collagen acts to hold the water against the skin cells allowing the skin cells to rehydrate without clogging the pores of the skin.

The product disclosed and described herein is an effective treatment to replenish to skin from moisture loss due to the drying effects of sun, wind, heat, cold, air-born impurities and toxin. It lets you replenish the loss anywhere right on the spot by simply spraying the formula directly on the skin. There is no rubbing or any other particular activity or time needed for application. Further, only the proper pre-mixed amount is applied to the skin. There is no waste or overuse typical of creams or lotions which results in excessive costs and wastes money. The formulas disclosed herein are a perfect suplement to any skin care program that women might use and will not disturb hair, make-up or clothing. It is particularly ideal for use immediately after applying make-up to help seal and set the make-up for the day.

This invention is not to be limited by the embodiment described in the description which is given by way of example and not of limitation, but only in accordance with the scope of the appended claims.

What is claimed is:

1. A skin moisturizing spray composition comprising;
   a mixture consisting essentially of a water soluble animal collagen in the range of 1% to 2% with water in the range of 98% to 99%;
   whereby said mixture can be applied to the skin in a fine mist spray with said water soluble collagen binding said water to moisturize the skin.

2. The skin moisturizing spraying composition according to claim 1 in which said water is pure deionized water.

3. The skin moisturizing spray composition according to claim 2 in which said mixture comprises; approximately 98.7% deionized water; approximately 1.8% water soluble animal collagen; and 0.3% DMDM hydantoin.

4. The skin moisturizing spray composition according to claim 1 including DMDM Hydantoin in the range of approximately 0.03% to approximately 0.05% as a preservative.

5. The skin moisturizing spray composition according to claim 1 including approximately less than about 2% cucumber extract.

6. The skin moisturizing spray composition according to claim 4 including approximately less than about 2% cucumber extract.

7. The skin moisturizing spray composition according to claim 6 in which said cucumber extract is in the range of approximately 1% to approximately 2%.

8. The skin moisturizing spray composition according to claim 4 including approximately 1.5% Panthenol.

9. The skin moisturizing spray composition according to claim 8 in which said Panthenol is in the range of approximately 0.5% to approximately 1.5%.

10. A method of moisturizing the skin comprising;
    mixing a water soluble animal collagen in a range of approximately 1% to 2% with water in a range of 98% to 99%;
    filling a container having a spray means selected to produce a fine mist spray;
    spraying said mixture of water soluble animal collagen and water directly on the skin in a fine mist spray;
    whereby said water soluble animal collagen binds and retains said water to moisturize the skin.

11. The method according to claim 10 in which said mixed formula includes about 0.03% to 0.05% DMDM Hydantoin as a preservative.

12. The method according to claim 10 in which said water in said mixed formula is a Deionized Water.

* * * * *